United States Patent
Maschke et al.

(10) Patent No.: US 8,727,618 B2
(45) Date of Patent: May 20, 2014

(54) ROBOTIC DEVICE AND METHOD FOR TRAUMA PATIENT DIAGNOSIS AND THERAPY

(75) Inventors: Michael Maschke, Lonnerstadt (DE); Oliver Meissner, Munich (DE)

(73) Assignee: Siemens Aktiengesellschaft, München (DE)

( * ) Notice: Subject to any disclaimer, the term of this patent is extended or adjusted under 35 U.S.C. 154(b) by 609 days.

(21) Appl. No.: 11/603,617

(22) Filed: Nov. 22, 2006

(65) Prior Publication Data
US 2008/0118035 A1    May 22, 2008

(51) Int. Cl.
*H05G 1/02* (2006.01)

(52) U.S. Cl.
USPC .............................................. 378/197; 378/4

(58) Field of Classification Search
USPC ....................... 378/4–20, 195–197
See application file for complete search history.

(56) References Cited

U.S. PATENT DOCUMENTS

| | | | |
|---|---|---|---|
| 4,095,110 A * | 6/1978 | Bunch | 378/26 |
| 5,627,873 A * | 5/1997 | Hanover et al. | 378/197 |
| 5,848,126 A * | 12/1998 | Fujita et al. | 378/195 |
| 5,919,135 A * | 7/1999 | Lemelson | 600/407 |
| 6,221,012 B1 | 4/2001 | Maschke et al. | |
| 6,416,219 B1 * | 7/2002 | Pflaum et al. | 378/209 |
| 6,435,715 B1 * | 8/2002 | Betz et al. | 378/197 |
| 6,609,826 B1 * | 8/2003 | Fujii et al. | 378/198 |
| 6,720,966 B2 * | 4/2004 | Barth et al. | 345/424 |
| 6,823,207 B1 * | 11/2004 | Jensen et al. | 600/427 |
| 6,990,368 B2 * | 1/2006 | Simon et al. | 600/425 |
| 7,505,358 B2 | 3/2009 | Jang | |
| 7,508,913 B2 | 3/2009 | Boese et al. | |
| 2001/0005410 A1 * | 6/2001 | Rasche et al. | 378/197 |
| 2004/0001571 A1 | 1/2004 | Jahrling | |
| 2004/0013239 A1 * | 1/2004 | Gregerson et al. | 378/197 |
| 2004/0170254 A1 * | 9/2004 | Gregerson et al. | 378/197 |
| 2005/0041775 A1 * | 2/2005 | Batzinger et al. | 378/59 |
| 2005/0207526 A1 * | 9/2005 | Altman | 378/20 |
| 2005/0226377 A1 * | 10/2005 | Wong et al. | 378/65 |
| 2006/0120507 A1 | 6/2006 | Brunner et al. | |
| 2007/0003014 A1 | 1/2007 | Boese et al. | |
| 2007/0014391 A1 * | 1/2007 | Mostafavi et al. | 378/63 |
| 2007/0070714 A1 | 3/2007 | Jang | |

FOREIGN PATENT DOCUMENTS

| | | |
|---|---|---|
| DE | 102 11 081 A1 | 10/2003 |
| DE | 10 2004 057 308 A1 | 7/2006 |

OTHER PUBLICATIONS

Krötz, M. et al., "Interdisziplinäre Schockraumversorgung: Personelle, apparative und räumlich-logistische Konzepte in 3 Traumakrankenhäusern in Europa," *Der Radiologe*, Jul. 2002, Springer-Verlag 2002, pp. 522-532.

Linsenmaier, U. et al., "Strukturierte radiologische Diagnostik beim Polytrauma," *Der Radiologe*, Jul. 2002, Springer-Verlag 2002, pp. 533-540.

* cited by examiner

*Primary Examiner* — Hoon Song
(74) *Attorney, Agent, or Firm* — Lempia Summerfield Katz LLC (57) ABSTRACT

A medical treatment suite and method of use is described, having a projection X-ray apparatus mounted to a robot. The robot positions the projection X-ray apparatus with respect to a patient and data is taken in a form that is suitable for synthesizing computed tomographic images. The patient may be supported by a patient support apparatus, which may be mounted to another robot, which cooperates with the other robot so as to position the patient according to a selected treatment protocol. Each of the robots may be mounted to one of a floor, a ceiling or a wall of the room.

23 Claims, 4 Drawing Sheets

ROBOTIC DEVICE AND METHOD FOR TRAUMA PATIENT DIAGNOSIS AND THERAPY

TECHNICAL FIELD

The present application relates of an apparatus and method for assisting in the diagnosis and treatment of traumatic injuries.

BACKGROUND

Fast, reliable, imaging diagnosis and suitable treatment for emergency and trauma patients is still among the major logistical challenges for the clinical environment. When a medical emergency occurs, and particularly when a patient has multiple injuries, the earliest possible diagnosis and treatment is particularly important. For this reason, the first few hours after a patient arrives at a medical facility, perhaps in shock, are called the "golden hours", as the effective use of this time is often of decisive importance for the further clinical course of the patient.

Best practices in emergency medical treatment management may involve interdisciplinary collaboration of anesthesia, radiology and trauma surgery, with the goal of diagnosing life-threatening injury patterns rapidly and promptly and contemporaneously initiating appropriate therapeutic actions. In the initial phase of emergency medical care, a team of 10-15 doctors, nurses and technicians can be involved. A wide variety of medical diagnostic equipment, techniques and protocols can be needed, depending on the nature of the medical emergency or injury.

Imaging modalities used for diagnostics are an essential component of the initial clinical phase of care. The relevant injuries or conditions should be diagnosed quickly and reliably, and life-saving therapeutic treatment is sometimes initiated and performed even during the ongoing imaging diagnostics. Moreover, the use of radiological interventional methods, such as balloon occlusion or CT-controlled ventricle catheter system for treating brain swelling, may be desirable.

Often, a trauma patient must be taken to a CT (computed tomography) examination room so that a complete imaging diagnosis can be made. The patient may then be returned to the trauma treatment room for further treatment or taken to another treatment room. Moving the patient between the various diagnostic equipment location wastes time during the "golden hour".

Some more efficient arrangements for diagnosis and treatment in the trauma or emergency room do exist. For instance, with the Siemens AXIOM Vertix MD Trauma, it is possible to obtain digital 2D projection radiography images of the patient directly in the trauma room. This has the advantage of immediate availability and relatively effective physical access to the patient. A disadvantage is the restriction of the technology to 2D projection images.

From US Pg-Pub No. 2004/0001571 "System for Emergency Medical Care and Monitoring of a Patient"; a combination system of a computed tomography (CT) and a conventional 2D X-ray system is known. This approach permits use of computed tomographic imaging, partially 3D cross-sectional images, and the additional capability of analog 2D projection images made directly in the trauma room. From "Interdisziplinäre Schockraumversorgung: Personelle, apperative und räumliche-logische Konzepte in 3 Traumkrankenhäusern in Europa" ["Interdisciplinary Trauma Room Care: Concepts with Regard to Personnel, Equipment and Space Logistics in 3 Trauma Hospitals in Europe"], Der Radiologe 7-2002 and "Strukturierte radiologische Diagnostik beim Polytrauma" ["Structured Radiological Diagnostics in Polytrauma"], Der Radiologe 7-2002, principles are likewise described for improving patient care. However, these solutions to the problem have a disadvantage that a relatively large space is needed for the equipment and the necessary repositioning of the patient during the individual steps in examination, the limited capability of direct radiologically managed intervention, or the lack of capability of, for example, angiographic intervention. In existing equipment, analog imaging technologies may result in a further delay, in some circumstances, for the development of photographic material.

In co-pending U.S. patent application, Ser. No. 11/478,087, by J. Boese and B. Heigl, a floor-mounted robot with a C-arm X-ray system is described. System concepts are described with which a patient can be repositioned using a floor-mounted robot and a diagnostic X-ray examination can be performed using a floor- or ceiling- mounted C-arm X-ray system (radiation emitter and detector combination). These concepts, however, do not extend to the clinical emergency and trauma processes and are restricted to uses of X-ray examination or therapy. Mobile C-arm X-ray diagnostic equipment has been developed for this purpose, and has become well known in the medical art of surgical and other interventional procedures.

A C-arm X-ray configuration refers to C-shaped structural member having an X-ray source and an X-ray detector typically mounted at or near the ends open ends of the "C" such that a central ray of the X-radiation is orthogonal to the surface of a facing X-ray detector. The space within the C-shape of the arm and the aperture to the "C" provides room maneuvering the patient, or for the physician to attend to the patient with minimal interference from the X-ray support structure.

The C-arm can be mounted to permit rotational movement of the arm about two perpendicular axes in a spherical motion. The entire C-arm may also be translated in linear directions to facilitate positioning with respect to the patient.

When the C-arm X-ray system uses a real-time X-ray detector, the C-arm may be rotated about the patient so that computed tomography (CT) images may be obtained. In such a use, image data acquisition may take approximately 10 seconds with C-arm rotation through approximately 200 degrees.

Digital detector systems for projection radiography are becoming commonplace in the clinical environment, and may be used to facilitate the rapid acquisition of data with the C-arm system. Such digital detectors provide high spatial resolution while having a high quantum efficiency. Apart from reducing the patient radiation dosage, such detectors may be highly linear and have sufficient resolution and dynamic range to be used in CT applications.

Figure 3:
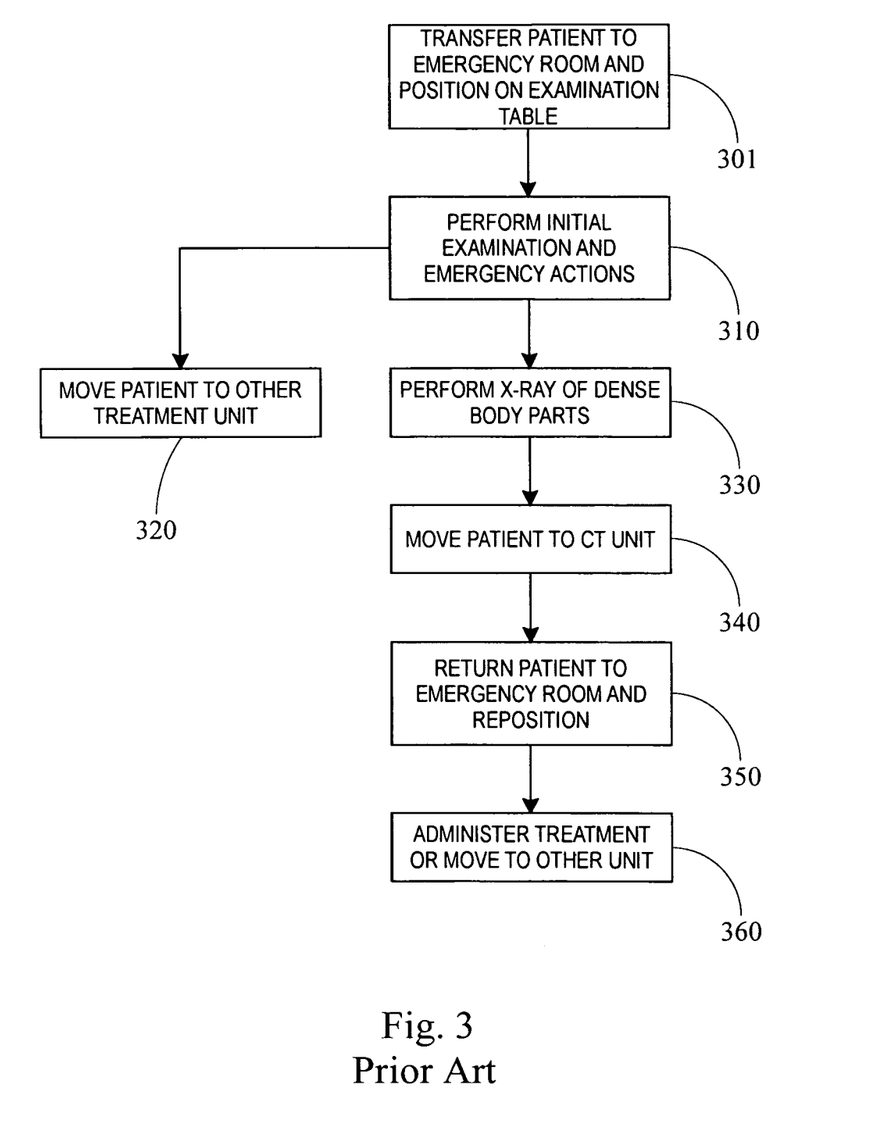
FIG. 3 is a block diagram of a prior art method of treating a patient having a medical emergency.

FIG. 3 is a flow chart of one possible sequence of steps and procedures which may be performed in a trauma or emergency room. The number of steps, the type of diagnostic or treatment procedure employed depends on the nature of the injury or illness that has resulted in the patient being brought to the hospital.

When a patient has been brought to an emergency room (step 301), initial clinical examination and emergency action required by the circumstances presented is performed (step 310), such as intubation, patient monitoring, and in some cases the nature of the emergency is such that a determination of the next treatment steps can be made by a doctor or the like, such as immediate transfer to a treatment room or to a specialized diagnostic room (step 320). Otherwise, a series of actions are performed based on accepted medical practice so as to determine the nature and severity of the trauma, and to initiate an appropriate course of treatment. The actions may include the moving the patient to an X-ray machine (step 330), so as to determine if there is an injury to the bones, and to a CT machine (step 340) to obtain projection radiographic images so that a computed tomography (CT) image of a portion of the patient may be produced for diagnostic purposes. In the case of steps 330 and 340, the patient may have to be repositioned and moved outside the emergency room so that the X-ray or CT equipment may be employed. Subsequent to obtaining the X-ray or CT images, the patient may be returned to the emergency room (step 350). Sometimes these steps may have to be repeated if the data obtained is unsatisfactory or incomplete. Moving a patient takes time, and is particularly awkward when the patient is encumbered by intubation, or other monitors or treatment apparatus. After diagnostic data is obtained and interpreted, the patient is either treated in the emergency room or transferred to an interventional unit, a surgical unit or other care provider station (step 360).

The frequent movement of a patient between the various diagnostic devices takes time and personnel. Such movement also means that not all of the emergency room facilities are available at all times during the diagnostic period.

SUMMARY

A diagnosis or therapy unit is described, including an imaging modality, such as a C-arm X-ray device, capable of recording projection radiographic data. The imaging modality is attached to a robot which may be mounted on a surface of a room; the unit is operated to collect radiographic and other data of a patient. A processor is configured to synthesize three-dimensional images or other images, such as are known in computed tomography (CT) from the data. The robot positions the imaging modality with respect to the patient in accordance with an operator input, or in accordance with an examination or treatment protocol.

A method of diagnosing or treating a patient is disclosed, including providing a projection X-ray radiographic apparatus. The X-ray apparatus is mounted to a robot, the robot being mounted to one of the interior surfaces of a room. The radiographic apparatus is operated so as to obtain a plurality of images of a patient suitable for synthesis of a computed tomography (CT) image.

A process for diagnosing or treatment of a patient is disclosed including moving the patient to a trauma room and positioning the patient on an examination table. A robotically mounted imaging devices is positioned and operated to obtain data suitable for producing computed tomography images of at least one of the hard body parts or soft body tissue, and the treatment protocol is administered at least in part while the patient remains in the trauma room.

DETAILED DESCRIPTION

Exemplary embodiments may be better understood with reference to the drawings. Like numbered elements in the same or different drawings perform equivalent functions.

In the interest of clarity, not all the routine features of the examples herein are described. It will of course be appreciated that in the development of any such actual implementation, numerous implementation-specific decisions must be made to achieve a developers' specific goals, such as compliance with system and business related constraints, and that these goals will vary from one implementation to another.

A robot-based emergency room or trauma room for examination and treatment of emergency and (poly)trauma patients directly in the trauma room is described. The imaging modality used may be a C-arm X-ray unit or other imaging modalities, such as an ultrasound device, or the like, or later developed imaging technologies capable of acquiring projection image data suitable for synthesizing CT-like images.

The combination of hardware and software to accomplish the tasks described herein may be termed a platform or "therapy unit". The instructions for implementing processes of the platform may be provided on computer-readable storage media or memories, such as a cache, buffer, RAM, removable media, hard drive or other computer readable storage media. Computer readable storage media include various types of volatile and nonvolatile storage media. The functions, acts or tasks illustrated or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Some aspects of the functions, acts, or tasks may be performed by dedicated hardware, or manually by an operator.

The instructions may be stored on a removable media device for reading by local or remote systems. In other embodiments, the instructions may be stored in a remote location for transfer through a computer network, a local or wide area network, by wireless techniques, or over telephone lines. In yet other embodiments, the instructions are stored within a given computer, system, or device.

Where the term "data network", "web" or "Internet" is used, the intent is to describe an internetworking environment, including both local and wide area networks, where defined transmission protocols are used to facilitate communications between diverse, possibly geographically dispersed, entities. An example of such an environment is the world-wide-web (WWW) and the use of the TCP/IP data packet protocol, and the use of Ethernet or other known or later developed hardware and software protocols for some of the data paths.

Communications between the devices, systems and applications may be by the use of either wired or wireless connections. Wireless communication may include, audio, radio, lightwave or other technique not requiring a physical connection between a transmitting device and a corresponding receiving device. While the communication is described as being from a transmitter to a receiver, this does not exclude the reverse path, and a wireless communications device may include both transmitting and receiving functions.

A diagnostic device has at least one X-ray source and at least one X-ray detector. The X-ray source may be mounted to a first robot and the X-ray detector to a second robot. In another example, the X-ray source may be fastened to a C-arm, U-bracket or any other kind of fastening jointly with the X-ray detector, and may be secured to a robot. Robots may be fixedly mounted to surface such as a ceiling, wall or floor, be captivated to and guided in the one or more dimensions on a rail structure, be mounted on wheels, or the like. The term "mounted to a surface" should be understood to include a wheeled mounting arrangement held in contact with the floor by the force of gravity.

Further, the diagnostic device may have a stretcher or gurney, or provisions for mounting the same, or other patient support apparatus. The patient support apparatus may be made of materials that are substantially transparent to X-rays. The patient support apparatus may be positionable manually or by a motor or hydraulic mechanism in various coordinate orientations such as height, and longitudinal and transverse directions, and may be inclined in any of the directions, rotated about a center point, or execute circular, elliptical, or other rotary motions about a specified point or in a specified plane. The patient support apparatus may be mounted to a third robot, which may be mounted to a floor, a wall or a ceiling. Alternatively, the robot may be movable with respect to a surface such as the floor so as to facilitate transferring the patient between treatment stations or rooms. The robot may further be capable of transferring the patient to another patient support apparatus, an operating table, or the like.

The imaging modality of the diagnostic device may further comprise an X-ray tube, radiation aperture, X-ray detector, digital imaging system, system controller, and a collision monitoring unit, as well as user control and display units. The X-ray detectors may be amorphous Silicon (a-Si) amorphous Selenium (a-Se), PbI2, CdTe or HgI2 detectors, or the like, using direct detection or TFT technology, or indirect detectors as is known in the art, or may be subsequently developed, to provide high resolution, high-dynamic-range essentially real-time X-ray detection. The X-ray detector may have a generally flat-panel aspect and a rectangular or square shape. The X-ray source may be rotated around the patient along a circular or elliptical path. The X-ray detector may be disposed diametrically opposed to the X-ray source and such that the plane of the detector is perpendicular to the axis of the X-ray source. This orientation may, for example, be maintained by attaching the X-ray source and X-ray detector to a C-arm, a U-arm or the like. This configuration produces a projection-type image.

The imaging device is operated by rotating, for example, the C-arm such that the opposed X-ray source and X-ray detector traverse an angular range of at least about 180 degrees about an axis perpendicular to the plane of the C-arm. A CT-like image may be reconstructed from the detected X-ray data. For example, a soft tissue image may be reconstructed using the methods described in US Pg-Pub US 2006/0120507 entitled "Angiographic X-ray Diagnostic Device for Rotational Angiography, filed on Nov. 21, 2005", which is incorporated herein by reference. The algorithmic and measurement aspects of computed tomography images are being improved, and the processing of the images obtained by the imaging devices are expected to continue to improve in resolution and dynamic range, speed, and in reduction of the X-ray dosage.

The term "X-ray" is used to describe any device that uses ionizing radiation to obtain data regarding the opacity of a path through a patient, regardless of the wavelength of the radiation used.

Image quality may also be improved by the use of an electrocardiogram (EKG) or respiration-controlled processing of the 2-D projection images used for the synthesis of CT-like images, or for 4D images (that is, time varying 3D images). One method of using bodily function monitors such as an EKG or respiration monitor is to select the images to be used in the synthesis of a 3D image from portions of the data set corresponding to similar stages of a heart or respiration cycle. Such digital processes do not, however, exclude the use of X-ray film (in an X-ray cassette).

Where the treatment room makes used of automated or machine-guided movements of the various pieces of examination or treatment apparatus, a collision avoidance system may be used to prevent injury to the patient or apparatus by determining the relative positions of the equipment pieces with respect to each other and to the patient. Such a collision avoidance system may use ancillary equipment such as ultrasonic or optical sensors, determinations of the equipment locations from the equipment controls, and the system knowledge of the equipment and patient positions relative to a baseline. Whichever combination of hardware and software is used is intended to maintain the location of the various objects to avoid unwanted contact, and to immobilize the equipment when a dangerous situation is encountered. This action may be preceded by one or more types of warning messages or sounds.

The user control units may include selection of examination or treatment options (so-called organ or examination programs). If an examination program for the thorax is selected, for example, the system components, image processing and the associated emitters, and detector and patient support apparatus positions may be automatically adjusted by a system controller to be positioned and configured to perform the predetermined examination protocol.

The examination and treatment suite may include a DICOM (Digital Communication in Medicine) interface including MPPS (Modality Performed Procedure Step), having the capability of further processing the image information and patient data, and interfacing with a data network.

An emergency or trauma room may have additional treatment and diagnostic equipment such as a ventilator, a patient monitor, which may be a mobile patient monitor as in U.S. Pat. No. 6,2221,012, "Transportable Modular Patient Monitor with Data Acquisition Modules"), a defibrillator, a mobile medication and instrument cabinet, a data terminal for inputting and outputting patient data, such as demographic data, insurance card, laboratory data, patient history and diagnosis information (for example, in the form of a "wireless notebook PC" or the like), various video displays for displaying data and images, and a digital camera unit for monitoring and video documentation of the individual diagnostic and therapeutic steps.

When a patient having an emergency or trauma is brought to the treatment room, the robotic aspects of the system may be used to efficiently transfer the patient between the various examination and treatment stations, including moving the patient to another room. A robotic arm may facilitate rapid and precise positioning of an imaging device such as the C-arm X-ray device for the specific examination or treatment protocol selected.

Further, robotically controlled positioning of the diagnosis equipment with respect to the patient allows diagnostics of, for example, both the body trunk and outer extremities in one examination sequence. Thus, a complex lower leg fracture, for instance, can be examined efficiently with 3D imaging, without moving the patient to another imaging device such as a CT.

With a robot-based C-arch system, such diagnostic procedures as angiographic 2D/3D images of the vessels with the capability of direct intervention can be done directly in the trauma room.

Figure 1:
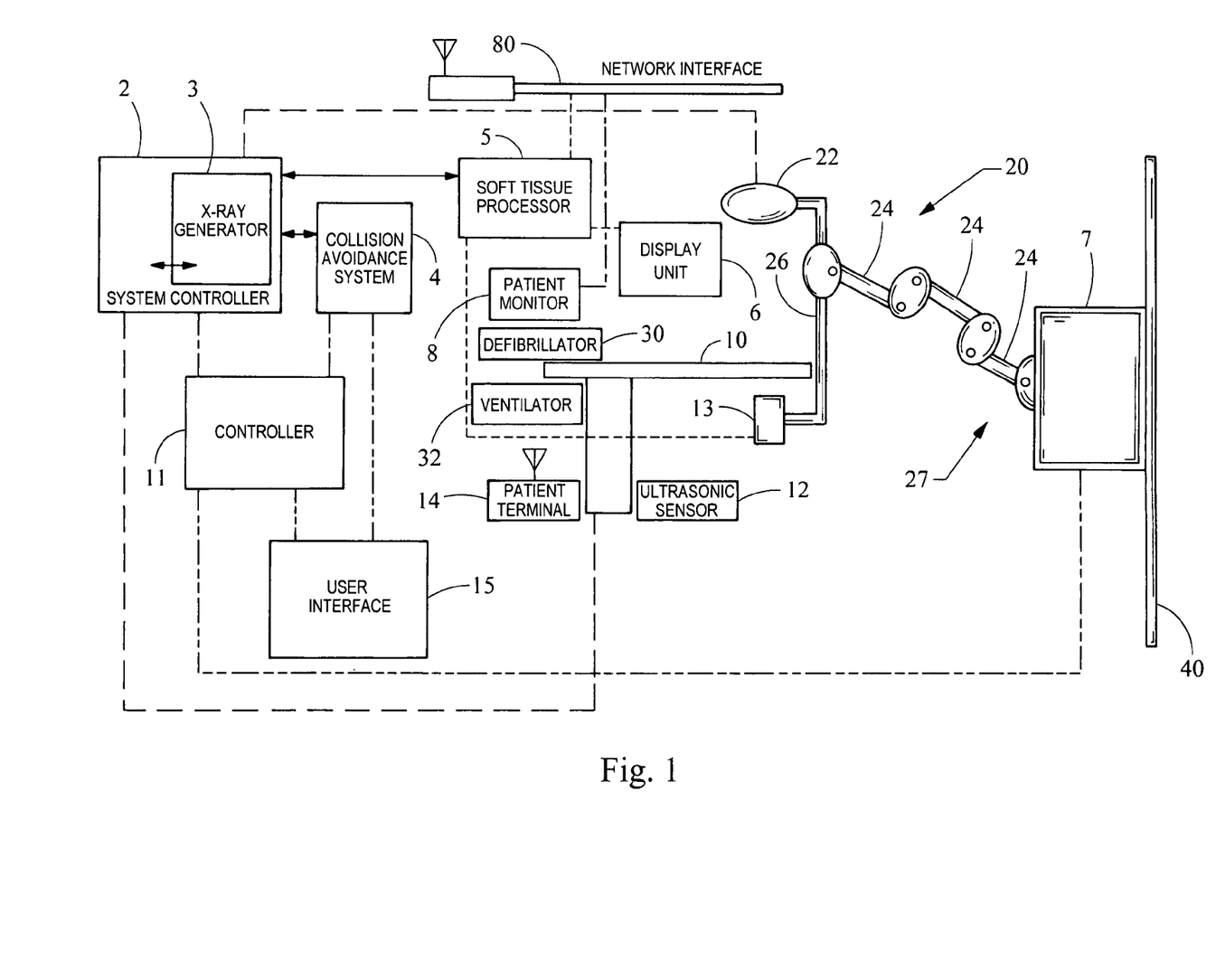
FIG. 1 is a block diagram of an example of a robotically positioned projection X-ray apparatus and related diagnostic and treatment devices.

FIG. 1 shows a block diagram of an example of a trauma diagnostic or therapy unit ("therapy unit") having a robotically-positioned projection X-ray apparatus and ancillary equipment. Other embodiments of the therapy unit may include fewer than all of the devices, or functions, shown in FIG. 1. A C-arm X-ray device 20 is representative of the imaging modalities which may be used and comprises a C-arm support 26 to which an X-ray source 22, which may include a diaphragm to limit the field of view, and an X-ray detector 13 may be mounted so as to face each other along a central axis of radiation. The C-arm 26 is mounted to a robotic device 27 comprising a mounting device 7, and one or more arms 24 which are articulated so as to be capable of positioning the C-arm X-ray device with respect to a patient support apparatus 10. The robotic device 27 may be controlled by a controller 11, which may send commands causing a motive device (not shown) to move the arms 24. The motive device may be a motor or a hydraulic mechanism. The mounting device may be mounted to a wall 40 as shown, to a ceiling or to a floor, and may be capable of moving in a longitudinal and transverse directions with respect to the mounting surface.

The C-arm X-ray device 20 is rotatable such that a plurality of projection X-ray images may be obtained by an X-ray detector 13 positioned on an opposite side of the patient from the X-ray source 22, and the images are reconstructed by any technique of processing for realizing computed tomographic (CT) images.

Herein, the term computed tomographic (CT) images is used to describe cross-sectional, sectioned, angiographic, hard, or soft tissue tomographic images, or the like, comparable to those which may be obtained from, for example, CT equipment, and where the data from which the image is synthesized or reconstructed is a plurality of projection X-ray images.

The patient is not shown in FIG. 1, but would be positioned on the patient support apparatus 10. The patient support apparatus may be a stretcher, gurney or the like and may be attached to a robot (not shown) having similar characteristics to that associated with the X-ray device 20. The patient support apparatus may be substantially transparent to X-ray, so that the X-ray source 22 and the X-ray detector 13 may be disposed on opposite sides of the patient. Additional, different, or fewer components may be provided. The devices and functions shown are representative, but not inclusive. The individual units, devices, or functions may communicate with each other over cables or in a wireless manner, and the use of dashed lines of different types for some of the connections is intended to suggest that alternative means of connectivity may be used.

The C-arm X-ray radiographic unit and the associated image processing may produce angiographic, hard, and soft tissue tomographic images comparable to, for example, CT equipment, while permitting more convenient access to the patient for treatment procedures. A separate processor 5 may be provided for this purpose, or the function may be combined with other processing functions.

A ultrasonic sensor 12 may be provided on one or more of the devices in the equipment suite, so as to measure the relative distance between, for example, parts of the C-arm X-ray device 20 and the patient support apparatus 10, or other equipment so as to aid in avoiding undesired contact between the devices. The relative position data and the ultrasonic data may be communicated to a collision avoidance system 4 which may be configured to prevent unsafe positioning. The ultrasonic sensor 12 may also be used to supplement other determinations of relative position and aspect derived from sensors or controls in each of the relevant devices. The ultrasonic sensor 12 may be used as a positioning input, or a safety stop when the devices come closer than a pre-determined distance from each other.

The C-arm X-ray system 20 may be controlled by a system controller 2, which may also include the X-ray generator 3, or at least the high voltage power supply. Other devices that may be useful in diagnosis or treatment of a patient, such as a defibrillator 30, a patient monitor 8 for monitoring vital signs, and a ventilator 32 may also be included. One or more display units 6 may be provided for visualizing the CT images and other data obtained from the various components of the equipment suite, including the status of devices.

The robot 27 may be controlled by a controller 11, which receives data from a user interface 15, and which also may communicate with a DICOM system and with external devices over a network interface 80.

The some portions of the therapy unit, such as the C-arm X-ray, the robots and patient sensors, may be located in a therapy room, and some or all of the signal and data processing and data display may also be located in the therapy room; however, some the equipment and functionality may be remotely located. Such remote location is facilitated by high speed data communications on local area networks, wide area networks, and the Internet. The signals representing the data and images may be transmitted by modulation of representations of the data on electromagnetic signals such as light waves, radio waves, or signals propagating on wired connections.

The therapy unit may thus be located remotely from the specialists making the diagnosis and for determining the appropriate course of treatment. Of course, the specialists may be present with the patient as well.

Figure 2:
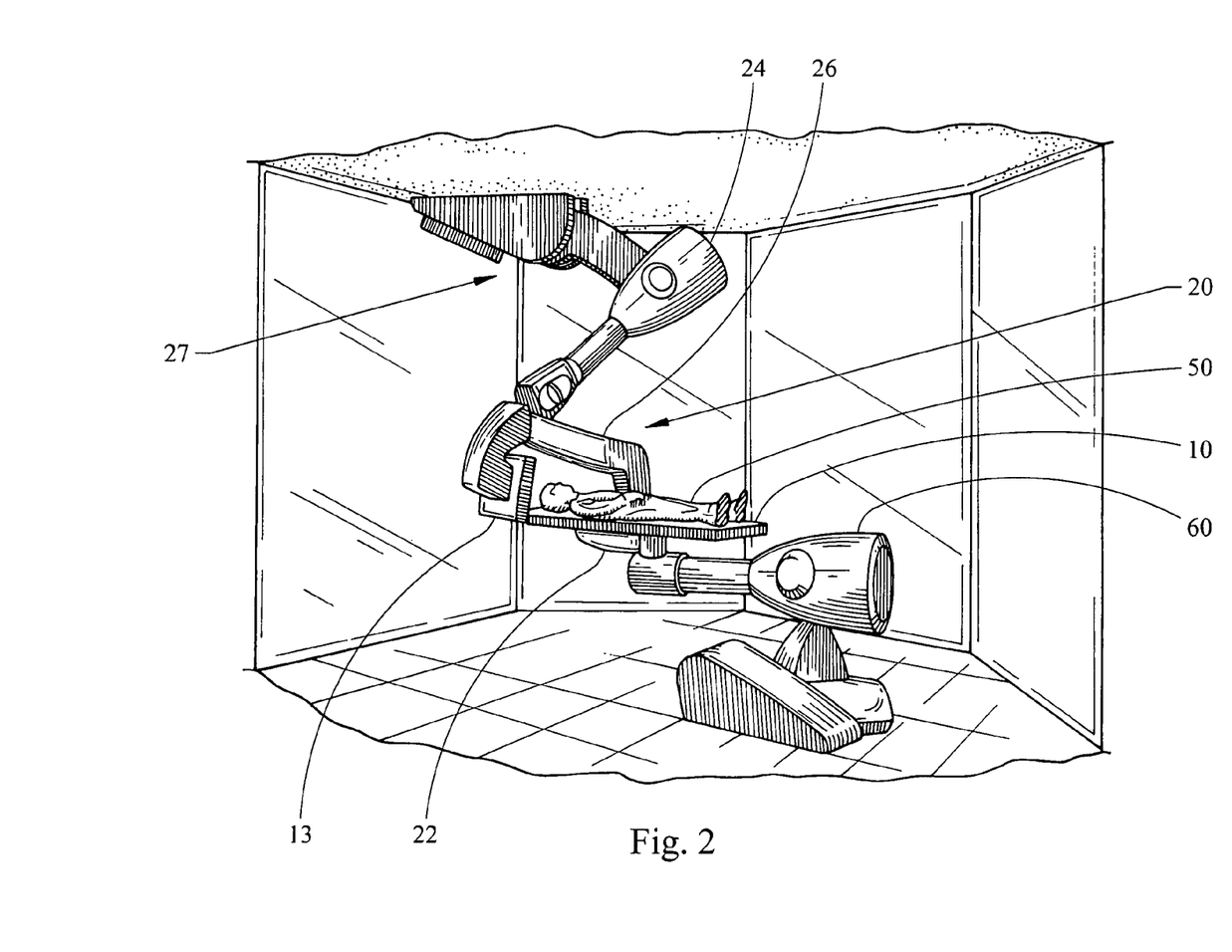
FIG. 2 is a perspective view of another example of a robotically positioned X-ray apparatus, where a patient support apparatus is positioned by a second robot.

FIG. 2 is a perspective view of some of the equipment which may be in a trauma diagnosis or therapy room. The robot 27 is mounted to a ceiling and supports and positions the C-arm X-ray device 20 by an articulated arm 24, so that the C-arm 26 and the associated X-ray source 22 and detector 13 may be suitably positioned with respect to a patient 50 on a patient support apparatus 10. The patient support apparatus 10 may also be mounted to a robotic device 60, which is shown mounted to the floor of the room, so that, cooperating with the robotic device 27, the C-arm X-ray device may be located such that the projection X-ray data to be used in synthesizing (computing) the computed tomography (CT) image may be obtained.

The patient terminal 14 may be a notebook computer, or other processing device with which the demographic, history, diagnosis and/or therapy data of the patient can be recorded, called up and sent to and from the medical information management system of the hospital. This device may communicate with other devices by wireless techniques.

Some or all of the data collected or processed by the equipment may be forwarded to another entity for use in diagnosis, billing and administrative purposes, or further image processing and storage using known interfaces such as DICOM ( Digital Communications in Medicine) and SOARIAN, or special purpose or later developed data formatting and processing techniques. SOARIAN is a web-browser-based information management system for medical use, integrating clinical, financial, image, and patient management functions and facilitating retrieval and storage of patient information and the performance of analytic tasks (available from Siemens Medical Solutions Health Service Corporation, Malvern, Pa.).

A method of diagnosing or treating a patient is disclosed, including: providing a projection X-ray radiographic apparatus, the apparatus being mounted to one or more robots mounted surfaces of a room; providing a patient support apparatus; orienting the radiographic apparatus with respect to a patient positioned on the patient support apparatus so as to obtain a sequences of projection radiographic images of a body part, suitable for synthesis of a computed tomography (CT) image.

The method may further include the mounting of the patient support apparatus on a another robot, the robot being mounted to one of the surfaces of the room, and controlling the robots so as to cooperatively position or reposition the patient so that image data consistent with a selected diagnosis protocol is obtained and processed.

In another aspect, the method may include mounting each of the X-ray source and the X-ray detector of the X-ray device to individual robots and operating the robots in a cooperative manner such that the robots are positioned so that image data consistent with a selected diagnosis protocol is obtained and processed A process for diagnosis or treating a patient in an emergency or trauma room using some or all of the equipment disclosed herein may include moving a patient to the emergency room and positioning the patient on an examination table. The patient may be intubated or connected to monitoring and treatment apparatus, and while remaining on the table, a projection radiographic X-ray device may be disposed with respect to the patient to obtain one or more X-ray images, which may include a sequence of images suitable for processing to produce computed tomography-like (CT) images. The images may be used to diagnose both bone and soft tissue injuries, and the patient may be treated while in the emergency room if such treatment is feasible. Positioning or repositioning of the patient may be facilitated by a robotically mounted X-ray device, by a robotically mounted examination table or both.

Figure 4:
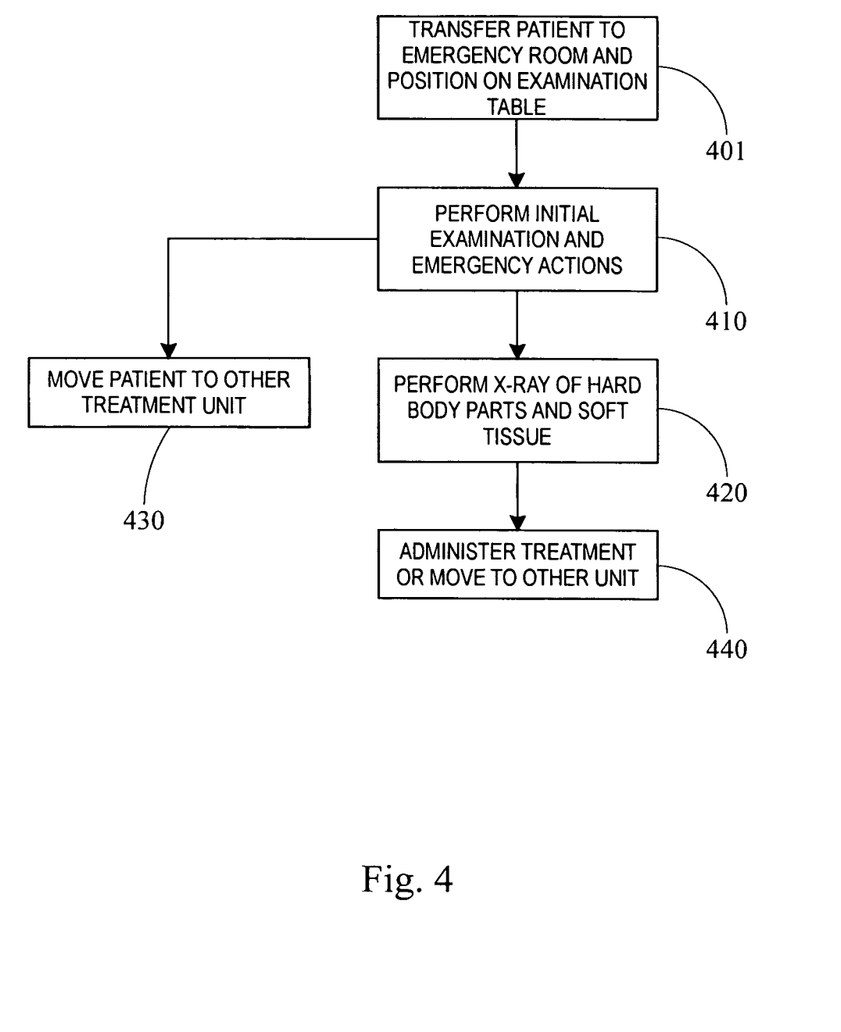
FIG. 4 is a block diagram of a method of treating a patient in an emergency room.

FIG. 4 illustrates an example of a sequence of steps which may be performed without moving the patient from the emergency room, although such movement is not precluded depending on the nature of the illness and the type of treatment that is determined to be medically necessary. In the situations where the patient can be diagnosed without leaving the emergency room, or be diagnosed and treated without leaving the emergency room, or where the number of movements outside the emergency room is minimized, the speed with which the injury or illness can be diagnosed or treated will be increased, thus improving the prognosis for a favorable outcome. The patient is transferred to the emergency room (step 401) and positioned on an examination table; after preliminary steps such as intubation or attachment of monitors (step 410), diagnostic images, such as projection radiographic images suitable for CT images are obtained (step 420). During, or as a result of steps 410 and 420 a medical decision may be taken to move the patient to another unit such as the surgical unit (step 430), or to treat the patient in the emergency room, which may involve obtaining further CT images or using the radiographic apparatus to guide another treatment device (step 440). All or some of the steps may be performed in the emergency room without moving the patient from the examination table. The minimization of patient movement and the speed of diagnosis are factors influencing the outcome of treatment; however, in some cases the course of diagnosis and treatment may be interrupted so as to move the patient to another unit. However, when diagnosis and treatment of the patient can be performed in accordance with the steps shown in FIG. 4, the result may be improved.

While the methods disclosed herein have been described and shown with reference to particular steps performed in a particular order, it will be understood that these steps may be combined, sub-divided, or reordered to from an equivalent method without departing from the teachings of the present invention. Accordingly, unless specifically indicated herein, the order and grouping of steps is not a limitation of the present invention.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. A diagnosis and patient care unit, comprising:
a C-arm X-ray apparatus having a C-arm structure, to which an ionizing radiation source and a radiation detector are mounted, such that the C-arm X-ray apparatus is configured to obtain projection-type image data;
a multi-axis robot operable to rotate the C-arm X-ray apparatus about two orthogonal axes;
a processor configured to synthesize tomographic images from the projection-type image data; and
further comprising two or more devices selected from:
an electrocardiogram (EKG) unit;
a respiration monitor;
a collision monitor;
a network interface configured to provide digital imaging in medicine (DICOM) functionality,
wherein the C-arm X-ray apparatus is mounted to the multi-axis robot so as to be positionable with respect to a patient support apparatus, the multi-axis robot having at least two rotation axes with different spatial directions; and
wherein the C-arm X-ray apparatus is operable to obtain image data to perform a diagnosis and determine where to treat an injury to a patient based on the diagnosis, the determination of where to treat the injury comprising the patient remaining on the patient support apparatus for a time duration of the diagnosis and at least a part of a time duration of the treatment.

2. The unit of claim 1, wherein the patient support apparatus is a gurney or a patient examination table mounted to a floor.

3. The unit of claim 1, wherein the patient support apparatus is adapted to support the patient and be positionable in one or more linear axes by a motor or a hydraulic mechanism.

4. The unit of claim 3, wherein the patient support apparatus is positionable in one or more axes of rotation.

5. The unit of claim 1, wherein the patient support apparatus is substantially transparent to X-radiation.

6. The unit of claim 1, further comprising the patient support apparatus.

7. The unit of claim 6, wherein the C-arm X-ray apparatus, the multi-axis robot, the patient support apparatus, or a combination thereof has a collision avoidance sensor.

8. The unit of claim 1, further comprising a processor configured to synthesize three dimensional (3D) soft-tissue images.

9. The unit of claim 1, further comprising: a soft-tissue computed tomography (CT) processor.

10. The unit of 9, wherein the data interface is configured to transmit data by modulating information on a carrier wave.

11. The unit of claim 1, wherein the multi-axis robot is configured to position the C-arm X-ray apparatus with respect to the patient support apparatus according to information relating to the treatment to be performed.

12. The unit of claim 11, wherein the multi-axis robot is configured by instructions stored on a machine readable media.

13. The unit of claim 1, wherein the multi-axis robot is mounted to a surface of a ceiling, a wall or a floor, and a mounting device is positionable in a longitudinal or transverse manner with respect to the mounting surface.

14. The unit of claim 1, wherein the multi-axis robot is configured as an articulated arm.

15. A method of caring for a patient, the method comprising:
    providing a projection C-arm X-ray apparatus rotatable in two orthogonal axes;
    mounting the projection C-arm X-ray apparatus to a first robot, the first robot being mounted to a surface of a room;
    orienting the projection C-arm X-ray apparatus with respect to a patient positioned on a patient support apparatus using the first robot;
    obtaining a plurality of radiographic images of a body part, the plurality of radiographic images being suitable for synthesis of a computed tomography (CT) image using the projection C-arm X-ray apparatus;
    using the CT image to diagnose a traumatic injury;
    determining where to treat the traumatic injury based on the CT image; and
    treating the traumatic injury without moving the patient from the patient support apparatus based on the determination of where to treat the traumatic injury,
    wherein the first robot is a multi-axis robot having at least two rotation axes with different spatial directions, and the treatment is aided by image data obtained by the projection C-arm X-ray apparatus.

16. The method of claim 15, wherein the patient support apparatus is mounted to a second robot, the second robot being mounted to the surface of the room.

17. The method of claim 15, wherein an ultrasonic sensor is used for avoiding a collision between any two of the projection C-arm X-ray apparatus, the first robot, the patient support apparatus and the patient.

18. The method of claim 15, further comprising selecting radiographic images from the plurality of obtained radiographic images for synthesis of the CT image using information on a bodily cycle obtained a respiration sensor, a electrocardiogaph (EKG), or a combination thereof.

19. A process of caring for a patient, the process comprising:
    moving the patient to a trauma unit;
    positioning the patient on an examination table;
    orienting and operating a robotically mounted C-arm X-ray apparatus to obtain computed tomographic (CT) images of the patient;
    processing the CT images to produce an image of dense body parts, an image of soft body tissue, or the image of dense body parts and the image of soft body tissue;
    performing a diagnosis of a traumatic injury of a plurality of traumatic injuries;
    determining a course of medical treatment for the diagnosed traumatic injury, determining the course of the medical treatment comprising determining where to treat the traumatic injury based on at least one of the CT images; and
    providing the medical treatment in whole or in part while the patient remains in the trauma unit based on the determination of where to treat the traumatic injury,
    wherein the C-arm X-ray apparatus is mounted to a multi-axis robot having at least two rotation axes with different spatial directions; and
    wherein the course of the medical treatment is performed entirely in the trauma unit.

20. The process of claim 19, wherein the patient is positioned with respect to the robotically mounted C-arm X-ray apparatus by the multi-axis robot, to which the C-arm X-ray apparatus is mounted, a robotic device, to which the examination table is mounted, or a combination thereof.

21. The process of claim 19, wherein the patient examination table is mounted to another robot that cooperates with the multi-axis robot so as to position the patient according to a selected treatment protocol of the course of the medical treatment.

22. The process of claim 19, wherein the medical treatment is controlled in whole or in part such that a person administering the medical treatment is not directly contacting the patient.

23. The process of claim 19, wherein determining the course of the medical treatment includes making a diagnosis of a syndrome using a CT image.

* * * * *